United States Patent [19]

von Eichborn et al.

[11] Patent Number: 4,946,674
[45] Date of Patent: Aug. 7, 1990

[54] PROCESS FOR TREATMENT OF RHEUMATIC DISEASES

[75] Inventors: Johann-Friedrich von Eichborn, Huttisheim; Hans-Joachim Obert, Laupheim; Franz Link, Bad Abbach, all of Fed. Rep. of Germany

[73] Assignee: Bioferon Biochemische Substanzen GmbH & Co., Laupheim, Fed. Rep. of Germany

[21] Appl. No.: 782,221

[22] Filed: Sep. 30, 1985

[30] Foreign Application Priority Data

Oct. 5, 1984 [DE] Fed. Rep. of Germany ....... 3436638
Jun. 18, 1985 [EP] European Pat. Off. ......... 85107490.6
Sep. 4, 1985 [EP] European Pat. Off. ......... 85111183.1

[51] Int. Cl.$^5$ ........................................... A61K 37/66
[52] U.S. Cl. .................... 424/85.5; 424/85.4
[58] Field of Search ........................ 424/85, 85.5, 85.4

[56] References Cited

U.S. PATENT DOCUMENTS

| | | | |
|---|---|---|---|
| 4,460,574 | 7/1984 | Yabrov | 424/85 |
| 4,480,032 | 10/1984 | Yabrov | 424/85 |
| 4,483,849 | 11/1984 | Carter et al. | 424/85 |
| 4,606,685 | 7/1984 | Vilcek et al. | 435/70 |
| 4,681,930 | 7/1987 | Kung et al. | 530/351 |
| 4,727,138 | 2/1988 | Goeddel et al. | 536/27 |

FOREIGN PATENT DOCUMENTS

| | | |
|---|---|---|
| 077063 | 4/1983 | European Pat. Off. |
| 77063 | 4/1983 | European Pat. Off. |
| 077670 | 4/1983 | European Pat. Off. |
| 87686 | 9/1983 | European Pat. Off. |
| 88540 | 9/1983 | European Pat. Off. |
| 107498 | 5/1984 | European Pat. Off. |
| 0107498 | 5/1984 | European Pat. Off. |
| 110044 | 6/1984 | European Pat. Off. |
| 0110044 | 6/1984 | European Pat. Off. |
| 117470 | 9/1984 | European Pat. Off. |
| 8301198 | 4/1983 | PCT Int'l Appl. |

OTHER PUBLICATIONS

Chemical Abstracts, vol. 102, Abstract No. 843945, 1985.
Chemical Abstracts, vol. 103, Abstract No. 109975t, 1985.
I. F. Barinskii et al., "Successful Therapy of Autoimmune Disease in NZB/W Mice with Interferon", *Chemical Abstracts*, 100, abstract 172939d, (1984).
R. C. Butler and D. H. Goddara, "Controversy in the Treatment of Rheumatoid Arthritis": *Lancet*, Aug. 4, 1984, pp. 278–279, (1984).
M. Degre et al., "Immune Interferon in Serum and Synovial Fluid in Rheumatoid Arthritis and Related Disorders", *Ann. Rheum. Dis.*, 42, pp. 672–676, (1983).
E. G. Engleman et al., "Treatment of NZB/NZW F1 Hybrid Mice with *Mycobacterium bovis* Strain . . . ", *Arthritis Rheum.*, 24, pp. 1396–1402, (1981).
I. Gresser, "Can Interferon Induce Disease?", *INF* 4 1982, I. Gresser, ed., Academic Press, pp. 95–127, (*Gresser II*).
J. J. Hooks et al., "Immune Interferon in the Circulation of Patients with Autoimmune Disease", *New Eng. J. Med.*, 301, pp. 5–8, (1979), (*Hooks et al. I*).
J. J. Hooks et al., "The Role of Interferon in Immediate Hypersensitivity and Autoimmune Disease", *Ann. N.Y. Acad. Sci.*, 350, pp. 21–32, (1980), (*Hooks et al. II*).
A. Kajander et al., "Interferon Treatment of Rheumatoid Arthritis", *Lancet*, May 5, 1979, pp. 984–985, (1979).
T. O. Rosenbach et al., "Interferon Triggers Experimental Synovitis and May Potentiate Auto-Immune Disease in Humans", *Clin. Rheum.*, 3, pp. 361–364, (1984).
G. Sonnenfeld et al., "Time and Dosage Dependencies of Immunoenhancement by Murine Type II Interferon Preparations", *Cell Immunol.*, 40, pp. 285–293, (1978).
M. L. Stephenson et al., "Immune Interferon Inhibits Collagen Synthesis by Rheumatoid Synovial Cells . . . ", *Chemical Abstracts*, 102, abstract 130150j, (1985).
M. L. Stephenson et al., "Immune Interferon Inhibits Collagen Synthesis by Rheumatoid Synovial Cells . . . ", *FEBS Lett.*, 180, pp. 43–50, (1985).
T. H. Bacon et al, "The Use of Interferon in Diseases of Uncertain Aetiology", In *Interferon*, vol. 4, N. B. Finter, ed., Elseiver, Amsterdam, pp. 226, 227 and 229, (1985).
D. Boraschi et al., "Interferon–Gamma Reduces Macrophage-Suppressive Activity by Inhibiting Prostaglandin $E_2$ Release and Inducing Interleukin 1 Production", *J. Immunol.*, 133, pp. 764–768, (1984).
T. C. Cesario, "The Clinical Implications of Human Interferon", *Medical Clinics of North America*, 67, pp. 1147–1162, (1983).
"Topical Formulations Containing Interferons for Treatment of Lupus Erythematosus", *Chemical Abstracts*, 103, citation No. 103:92861c, (1985).
"Genetech, Biogen Report New Advances in Anti-Cancer, AIDS", *Chemical Marketing Reporter*, Jun. 11, 1984, pp. 5, 26, (1984).
R. C. Chin et al., "The Absence of Gamma-Interferon (Gamma-IFN) and the Presence of High Levels of Inflammatory Mediators . . . ", Fed. Proc., 42, Abstract 3838, p. 947, (1983).
B. Combe et al., "Interleukin-2 in Rheumatoid Arthritis: Production of and Response to Interleukin-2 . . . ", (List continued on next page.)

*Primary Examiner*—Blondel Hazel
*Attorney, Agent, or Firm*—James F. Haley, Jr.; Leon R. Yankwich; Andrew S. Marks

[57] ABSTRACT

This invention relates to the treatment of rheumatic diseases. More particularly, this invention relates to processes and compositions for treating rheumatic diseases by administering to a patient a pharmaceutically effect amount of gamma interferon.

9 Claims, No Drawings

OTHER PUBLICATIONS

*Arthritis Rheum.*, Abstract, 27 (Suppl.), p. S55, (1984), [Combe I].

B. Combe et al., "Regulation of Natural Killer Cell Activity by Macrophages in the Rheumatoid Joint and Peripheral Blood", *J. Immunol.*, 133, pp. 709—713, (1984), [Combe II].

W. R. Fleischmann et al., "Demonstration of Potentiation of The Antiviral and Antitumor Actions of Interferon", *Meth. Enzymol.*, 79, pp. 432–440, (1981).

F. Hasler et al., "Analysis of the Defects Responsible for the Impaired Regulation of Epstein-Barr Virus-Induced B Cell . . . ", *J. Exp. Med.*, 157, pp. 173–188, (1983).

F. Hasler et al., "Analysis of the Defects Responsible for the Impaired Regulation of EBV-Induced B Cell . . . ", *J. Immunol.*, 131, pp. 768–772, (1983).

K. Itoh et al., "Depressed Natural Killer Activity in Rheumatoid Arthritis and Its in vitro Augmentation . . . ", *The Ryumachi*, 21, (Suppl.), pp. 69–74, (1981).

S. A. Jiminez et al., "Selective Inhibition of Human Diploid Fibroblast Collagen Synthesis by Interferons", *J. Clin. Invest.*, 74, pp. 1112–1116, (1984).

M. Lipinski et al., "Natural Killer and Killer Cell Activities in Pateints with Primary Immunodeficiencies or Defects in Immune Interferon Production", *Eur. J. Immunol.*, 10, pp. 246–249, (1980).

I. Mecs et al., "The Anti-Inflammatory Effect of Human Interferons in Mice", *Contr. Oncol.*, 20, pp. 221–223, (1984).

O. J. Mellbye et al., "Immunological Research and the Rheumatic Patient: Status and Perspectives in Some Major Areas", *Scand. J. Rheumatol.*, Supplement 53, pp. 64–84, (1984).

A. G. Mowat, "Slow-Acting Antirheumatic Drugs", *S. Afr. Med. J.*, 61, pp. 346–348, (1982).

"Inferferon Nomenclature", *Nature*, 286, p. 110, (1980), 13th Arztliche . . . , Nov. 25 und 26, 1983; Programmheft S. 8, 9, 22, (1983).

K. T. Pearlstein et al., "Purified Human Interleukin-2 Enhances Induction of Immune Interferon", *Cell. Immunol.*, 80, pp. 1–9, (1983).

C. M. Pearson et al., "Workshop IV. Aetiopathogenic Factors in Reiter's Syndrome", *Ann. Rheum. Dis.*, 38, Supplement, pp. 102–110, (1977), [Pearson I].

C. M. Pearson et al., "Adjuvant Arthritis: Immune Responses and Effects of Tilorone or Interferon . . . ", *Perspect. Inflammation Proc. Int. Meet. 3rd*, pp. 131–146, (1979), [Pearson II].

S. Pestka et al., "Definition and Classification of the Interferons", *Meth. Enzymol.*, 78, pp. 3–14, (1981).

O. T. Preble et al., "Systemic Lupus Erythematosus: Presence in Human Serum of an Unusual Acid-Lbile Leukocyte Interferon", *Science*, 216, pp. 429–431, (1982).

G. H. Reem et al., "Interleukin 2 Regulates Expression of Its Receptor and Synthesis of Gamma Interferon by Human T Lymphocytes", *Science*, 225, pp. 429–430, (1984).

*Scand. J. Rheumatol.*, Supplement 49, p. 59, (1983).

M. L. Thoman et al., "Deficiency in Suppressor T Cell Activity in Aged Animals", *J. Exp. Med.*, 157, pp. 2184–2189, (1983).

D. Wallach, "Regulation of Susceptibility to Natural Killer Cells' Cytotoxicity and Regulation of HLA Synthesis . . . ", *J. Interferon Res.*, 2, pp. 329–338, (1982), [Wallach I].

D. Wallach, "Interferon-Induced Resistance to the Killing by NK Cells: A Preferential Effect of IFN—", *Cell. Immunol.*, 75, pp. 390–395, (1983), [Wallach II].

PROCESS FOR TREATMENT OF RHEUMATIC DISEASES

TECHNICAL FIELD OF INVENTION

This invention relates to the treatment of rheumatic diseases. More particularly, this invention relates to processes for treating rheumatic diseases such as inflammatory rheumatism, degenerative rheumatism, extra-articular rheumatism and collagen diseases. According to this invention, natural or recombinant gamma interferons are used for the treatment of these rheumatic diseases.

BACKGROUND ART

Rheumatic diseases are a group of diseases that effect the musculo-skeletal and connective tissues of the body. Such diseases are characterized by chronic inflammation which often leads to permanent tissue damage, deformity, atrophy and disability. Rheumatoid arthritis, a progressive rheumatic disease, affects as many as 1–2% of all adults [P. D. Utsinger et al., *Rheumatoid Arthritis*, p. 140 (1985)].

Although their etiology is unknown, most rheumatic diseases are thought to be autoimmune diseases caused by a patient's altered immune response to as yet unidentified antigen or antigens [H.O. McDevitt and B. Benacerraf, "Genetic Control Of Specific Immune Responses", *Adv. Immunol.*, 11, p. 31 (1969)].

Rheumatic diseases may affect the joints, spinal cord, soft tissue or bone [H. Mathies, *Rheuma* ("Rheumatism") (1983)] and are classified as inflammatory rheumatism, degenerative rheumatism, extraarticular rheumatism or collagen diseases. Systemic *lupus* erythematosus, progressive systemic scleroderma, dermatomyositis, chronic polyarthritis, *psoriasis* arthropathica, muscular rheumatism, *periarthritis* humeroscapularis, *panarteriitis* nodosa, myositis, myogelosis, *arthritis* uratica and chondrocalcinosis are also rheumatic diseases [W. Pschyrembel, *Klinisches Worterbuch* ("Medical Dictionary") (1982)]. Juvenile chronic arthritis, which occurs in children and adolescents, differs from rheumatoid arthritis as seen in adults and can lead to impaired development and growth [B. Z. P. Anzell, "Juvenile Chronic Polyarthritis", *Arthr. Rheum. Supp.*, 20, pp. 176–80 (1977); H. Truckenbrodt, "Die Juvenile Chronische Arthritis Und Ihre Subgruppen" ("Juvenile Chronic Arthritis And Its Subgroups"), *Munch. Med. Wschr.*, 126, pp. 1076–78 (1984). Upon serological examination, the majority of patients diagnosed with clinical rheumatic disease test seropositive for rheumatoid factor, an abnormal gamma-globulin [R. B. Berkow et al. (Eds.), *The Merck Manual* (1982)].

Because the etiology of the majority of rheumatic diseases remains unknown, no cure for these diseases exists and effective agents are not conventionally available for treatment of a specific disease [K. Krüger, "Neue Therapieprinzipien In Der Rheumatologie" ("New Therapeutic Principles In Rheumatology"), Münch. Med. Wschr., 126, pp. 1084–86 (1984)]. Moreover, these agents typically must be administered over long periods of time and any therapeutic value is often diminished by adverse side effects.

Therapeutics used in the treatment of rheumatic diseases fall into two classes. The first class of therapeutics, symptomatic anti-rheumatics, act on the symptoms of the disease, exerting effects both upon and throughout the total course of administration. Such symptomatic anti-rheumatics include salicylic acid, glucocorticoids and non-steroidal anti-inflammatory agents, such as inodomethacin. The second class of therapeutics, base anti-rheumatics, act on the pathogenesis of the disease, exerting their effects only after the initial weeks of administration yet having effects lasting beyond the cessation of treatment. Such base anti-rheumatics include gold compounds, D-penicillamine, chloroquine, cortisones and immunosuppressants [H. Mathies, Rheuma, infra, p. 1; R. C. Butler and D. H. Goddard, "Controversy In The Treatment Of Rheumatoid Arthritis", Lancet, ii, pp. 278–79 (1984)].

These prior therapeutic agents are often characterized by adverse side effects. For example, those that are immunosuppressants may increase the patient's susceptibility to infection. And, therapies based on gold compounds, penicillamine or chloroquine may exert toxic effects on the patient's system.

Alpha interferon has been reported to be ineffective in the treatment of rheumatoid arthritis [A. Kajender et al., "Interferon Treatment Of Rheumatoid Arthritis", Lancet, i, pp. 984–85 (1979)]. This lack of efficacy may not be surprising because certain rheumatic diseases, such as rheumatoid arthritis, are characterized by an endogenous formation of interferons to which no therapeutic activity has been ascribed. Furthermore, in some cases, high circulating levels of interferons have been suggested without real clinical data as a factor contributing to the pathogenesis of rheumatic diseases [J. J. Hooks et al., "Immune Interferon In The Circulation Of Patients With Autoimmune Disease", *N. Engl. J. Med.*, 301, pp. 5–8 (1979); O. T. Preble et al., "Systemic Lupus Erythematosus: Presence In Human Serum Of An Unusual Acid-Labile Leukocyte Interferon", *Science*, 126, pp. 329–31 (1982); M. Degré et al., "Immune Interferon In Serum And Synovial Fluid In Rheumatoid Arthritis And Related Disorders", *Ann. Rheumatic. Dis.*, 42, pp. 672–76 (1973); A. M. Arvin and J. J. Miller, "Acid Labile α-Interferon In Sera And Synovial Fluids From Patients With Juvenile Arthritis", *Arthritis and Rheumatism*, 27, pp. 582–85 (1984); T. 0. Rosenbach et al., "Interferon Triggers Experimental Synovitis And May Potentiate Auto-Immune Disease In Humans", *Clin. Rheumatol.*, 3, pp. 361–64 (1984)].

To date therefore, conventional methods and therapeutic agents have not proved to be effective in the treatment of rheumatic diseases. Accordingly, the need exists for a process which avoids the disadvantages of these conventional methods and agents while providing effective treatment for rheumatic diseases.

DISCLOSURE OF THE INVENTION

The present invention solves the problems referred to above by providing a process for the treatment of rheumatic diseases. According to this invention, natural or recombinant gamma interferons are used in processes and compositions for treating rheumatic diseases. Advantageously, the processes and compositions of this invention are effective and are not beset by the variety of side effects which typically characterize conventional treatments of rheumatic diseases.

BEST MODE OF CARRYING OUT THE INVENTION

In order that the invention herein described may be more fully understood, the following detailed description is set forth.

In the description, the following terms are employed:

Gamma interferon or IFN-γ — In accordance with the interferon nomenclature announced in *Nature*, 286, p. 110 (1980) and recommended by the Interferon Nomenclature Committee in *Archives Of Virology*, 77, pp. 283–85 (1983). IFN-γ was originally referred to as "immune interferon".

IFN-γ is a lymphokine which is naturally produced in minute quantities together with other lymphokines by lymphocytes. It is primarily produced by T-lymphocytes, spontaneously or in response to various inducers such as mitogens, specific antigens or specific antibodies [W. E. Stewart, II, *The Interferon System*, pp. 148–49 (1981)]. IFN-γ is a glycoprotein having a molecular weight between 20,000 and 25,000 (or 17,000 in non-glycosylated form). IFN-γ has also been cloned and expressed in various host-vector systems. The nucleotide sequence of cloned IFN-γ indicates that it is composed of 143–46 amino acids.

As used in this application and claims, "IFN-γ" includes all proteins, polypeptides and peptides which are natural or recombinant IFN-γs, or derivatives thereof, and which are characterized by the biological activity of those IFN-γs against rheumatic diseases. These include IFN-γ-like compounds from a variety of sources such as natural IFN-γs, recombinant IFN-γs, and synthetic or semisynthetic IFN-γs.

Rheumatic Disease — Any disease which is (i) characterized by inflammation or degeneration of musculoskeletal or connective tissue structures of the body, particularly the joints, and including muscles, tendons, cartilage, synovia and fibrous tissues, (ii) accompanied by pain, stiffness or impairment of locomotion or function of those structures and, in some cases, (iii) often accompanied by serological evidence of rheumatoid factor.

Rheumatic diseases include, but are not limited to, inflammatory rheumatism, degenerative rheumatism, extra-articular rheumatism and collagen diseases. Examples of such diseases are systemic lupus erythematosus, rheumatoid arthritis or chronic polyarthritis, progressive systemic scleroderma, dermatomyositis, psoriasis arthropathica, muscular rheumatism, periarthritis humeroscapularis, panarthritis nodosa, myositis, myogelosis, arthritis uratica, chondrocalcinosis and juvenile chronic arthritis ("Stills disease").

This invention relates to processes and compositions for treating rheumatic diseases. The process of this invention comprises the step of treating a mammal in a pharmaceutically acceptable manner with a pharmaceutically effective amount of IFN-γ for a period of time sufficient to reduce the symptoms of the specific rheumatic disease.

The IFN-γs used in the processes and compositions of this invention may be produced by purification from natural sources using conventional techniques or produced by recombinant techniques.

For example, some established or transformed cell lines produce natural IFN-γ constitutively in vitro [N. Fujii et al., "Spontaneous Production Of γ-Interferon In Cultures Of T Lymphocytes Obtained From Patients With Behcet's Disease", *J. Immunol.*, 130, pp. 1683–86 (1983)]. A T cell hybridoma variant clone was also found to produce IFN-γ, together with other lymphokines, in response to stimulation with concanavalin A [A. Zlotnick et al., "Coordinate Production By A T Cell Hybridoma Of Gamma Interferon And Three Other Lymphokine Activities: Multiple Activities Of A Single Lymphokine?", *J. Immunol.*, 131, pp. 794–80 (1983)].

Among the IFN-γs useful in the processes of this invention are also the IFN-γs produced in vitro by a variety of cells in response to various interferon inducers. For example, these IFN-γs include IFN-γs produced in human buffy-coat leukocytes after exposure to phytohemagglutinin P, concanavalin A and staphylococcal enterotoxin A ("SEA"), M. deLey et al., "Interferon Induced In Human Leukocytes By Mitogens: Production, Partial Purification And Characterization", *Eur. J. Immunol.*, 10, pp. 877–83 (1980); in human splenocytes after stimulation with SEA, R. Devos et al., "Isolation And Characterization of IFN-Gamma mRNA Derived From Mitogen-Induced Human Splenocytes", *J. Interferon Res.*, 2, pp. 409–20 (1982); by an IL-2independent murine T cell line after stimulation by phorbol 12-myristate 13-acetate, W. R. Benjamin et al., "Production of Immune Interferon By An Interleukin 2-Independent Murine T Cell Line", *Proc. Natl. Acad. Sci. USA*, 79, pp. 5379–83 (1982); in lymphoid cells by using calcium ionophore A-23187, F. Dianzani et al., "Human Immune Interferon: Induction in Lymphoid Cells By A Calcium Ionophore", *Infection And Immunity*, 29, pp. 561–63 (1980); and in thymocytes, G. H. Reem et al., "Gamma Interferon Induction In Human Thymocytes Activated By Lectins and B Cell Lines", *Infection And Immunity*, 37, pp. 216–21 (1982). See also, Y. R. Yip et al., "Stimulation Of Human Gamma Interferon Production By Diterpene Esters", *Infection And Immunity*, 34, pp. 131–39 (1981); U.S. Pat. Nos. 4,376,821; 4,376,822 and 4,460,685 and European patent application No. 63,482.

These natural IFN-γs have been subsequently purified to some extent and partially characterized. See, for example, U.S. Pat. Nos. 4,289,690, 4,314,935 and 4,382,027; European patent application No. 87,686; O'Malley, "Affinity Chromatography Of Human Immune Interferon", *Methods in Enzymology*, 78, pp. 540–45 (1981), and Y. K. Yip et al., "Partial Purification and Characterization of Human γ (Immune) Interferon", *Proc. Natl. Acad. Sci. USA*, 78, pp. 1601–05 (1981).

IFN-γs useful in the processes of this invention may also be produced in large amounts by cloning and expression in various host/vector systems using recombinant DNA technology. See, e.g., European patent application No. 88,540; R. Derynck et al., "Human Interferon γ Is Encoded By A Single Class Of mRNA", *Nucleic Acids Research*, 10, pp. 3605–13 (1982); R. Derynck et al., "Expression Of The Human Interferon-λ DNA In Yeast", *Nucleic Acids Res.*, 11, pp. 1819–37 (1983); R. Devos et al., "In Vitro Translation And Characterization Of Human IFN-γ mRNA", *J. Clin. Hemator. Oncol.*, 11(4), p. 114 (1981); R. Devos et al., "Molecular Cloning Of Human Immune Interferon cDNA And Its Expression In Eukaryotic Cells", *Nucleic Acids Research*, 10(8), pp. 2487–501 (1982). See also, G. Simons et al., Gene, 28, pp. 55-64 (1984); S. J. Schaill et al., *Proc. Acad. Sci. USA*, 80, pp. 4654–58 (1983) and P. W. Gray et al., *Nature*, 295, pp. 503–08 (1982).

As a result of some of these methods, IFN-γ is present in the culture medium up to a concentration of more than 100,000 International reference units per milliliter (I.U./ml) or it is concentrated in the host itself, constituting up to 25% of the protein content of the cell.

The purification of IFN-γ from the preparations produced according to the above-described processes may be effected by means of one or a combination of the following conventional methods:

controlled pore glass (CPG) or silica gel
gel filtration (AcA 54 or Sephacel S200, for example)
ion-exchange chromatography (CM-Sepharose, phospho-cellulose or DEAE-cellulose)
affinity chromatography (Con-A-Sepharose, Poly-U-Sepharose or CU-chelate-Sepharose)
immune affinity chromatography using an anti-IFN-γ Sepharose column
HPLC (with reverse phase materials, for example).

Other purification methods are described in Y. K. Yip et al., "Partial Purification And Characterization Of Human Gamma (Immune) Interferon", *Proc. Natl. Acad. Sci. USA*, 78, pp. 1601–05 (1981), D. Novick et al., "Monoclonal Antibodies To Human Interferon-γ: Production, Affinity Purification And Radioimmunoassay", *EMBO Journal*, 2, pp. 1527–30 (1983) or West German patent DE No. 3136166 Al.

By means of such methods, alone or in any combination thereof, purification up to electrophoretic homogeneity is possible. While the average IFN-γ specific activity of such purified substances ranges between about 10 and 50 million International units per mg of protein, it is possible to obtain specific activities of up to 100 million to 200 million International units per mg of protein.

Clinical preparations used in the processes of this invention may contain between about 100,000 to 200,000,000 I.U. per mg of protein (1 μg of active substance contains up to 200,000 International reference units).

The processes and compositions of this invention may be used to treat any mammal, including humans. According to this invention, mammals are treated by the pharmaceutically acceptable administration of IFN-γ in a pharmaceutically effective dosage and for a period of time sufficient to reduce the symptoms of the specific rheumatic disease or to prevent their recurrence.

According to this invention, IFN-γ may be administered to the patient in any pharmaceutically acceptable dosage form including those which may be administered to a patient intravenously as bolus or by continuous infusion over a period of hours, days, weeks or months, intramuscularly — including paravertebrally and periarticularly — subcutaneously, intracutaneously, intra-articularly, intrasynovially, intrathecally, periostally, or by oral or topical routes.

Such dosage forms may include pharmaceutically acceptable carriers and adjuvants which are known to those of skill of the art. These carriers and adjuvants include, for example, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of IFN-γ may be selected from the group consisting of sodium carboxymethylcellulose, polyacrylates, polyoxyethylene-polyoxypropylene-block polymers, polyethylene glycol and wood wax alcohols. For all administrations, conventional depot forms may be used. Such forms include, for example, nano-capsules, micro-capsules, liposomes and plasters.

The most effective mode of administration and dosage regimen of IFN-γ will depend upon the type of rheumatic disease to be treated, the severity and course of that disease, previous therapy, the patient's health status and response to IFN-γ and the judgment of the treating physician. IFN-γ may be administered to the patient at one time or over a series of treatments.

Depending on the severity of the disease, 200 I.U. (20 ng) to 2,000 million I.U. (10 mg) may be administered to the patient over the course of treatment. Generally, therapy is commenced with low doses of IFN-γ. For example, an initial dose of IFN-γ is administered to the patient by, for example, injection or infusion. That initial dose should contain between about 20,000 to 2,000,000 I.U. (about 2 μg to 200 μg) of IFN-γ. For repeated administrations over several days, dosages may be administered on successive days, every two to six days, once a week, every two to four weeks or once a month, until a desired suppression of disease symptoms is observed. However, other dosage regimens are also useful. When the symptoms have been alleviated to the desired level, treatment may cease. Patients may, however, require intermittent treatment on a long term basis upon recurrence of disease symptoms.

In cases of severe rheumatic disease, an initial dose of 50,000 I.U. (approximately 5 μg) of IFN-γ may be administered to the patient daily, over the course of between about 1 to 12 weeks, until the patient's condition improves. In the absence of improvement, this initial daily dose may be doubled after every 3 to 5 days of administration.

Once improvement in the patient's condition has occurred, a maintenance dose of about 2,000,000 I.U. (approximately 200 μg) is administered about 3 times a week. Subsequently, the dosage and/or frequency of administrations is reduced, as a function of the symptoms, to a level at which the improved condition is retained. Typically, such a maintenance schedule may involve the administration of about 500,000 I.U. (approximately 50 μg) to the patient once or twice a week.

In less severe cases of rheumatic disease, an initial dose of 1 or 2 injections of between about 50,000 and 1,000,000 I.U. (approximately 5 to 100 μg) of IFN-γ typically provides effective symptomatic treatment.

According to an alternate embodiment of this invention, the effectiveness of the IFN-γ may be increased by administration serially or in combination with other interferons derived from natural sources or produced by recombinant techniques, other cell mediators formed by leukocytes or produced by recombinant techniques such as, for example, inter-leukin-1, interleukin-2, tumor necrosis factor, macrophage colony stimulating factor, macrophage migration inhibitory factor, macrophage activation factor, lymphotoxin and fibroblast growth factor. Alteratively, IFN-γ may be administered serially or in combination with conventional anti-rheumatic therapeutic agents or drugs such as, for example, thymus hormones.

In order that the invention described herein may be more fully understood, the following examples are set forth. It should be understood that these examples are for illustrative purposes only and are not to be construed as limiting this invention in any manner.

In the following examples, the IFN-γs used in the treatment of rheumatic diseases were either natural human IFN-γ or human IFN-γ produced by recombinant DNA techniques. The specific activity of the natural human IFN-γ was in the range of 2–20 ×106

I.U./mg of protein. Recombinant human IFN-γ was supplied by Biogen S.A., Geneva, for clinical testing. The specific activity of Biogen's recombinant human IFN-γ was in the range of $10-20 \times 10^6$ I.U./mg of protein.

These examples represent the results of treatment of various rheumatic diseases using natural or recombinant IFN-γ according to the processes of this invention. As demonstrated in these examples, the use of IFN-γ according to this invention was therapeutically effective in the treatment of inflammatory rheumatism, extra-articular rheumatism, degenerative rheumatism and collagen diseases.

These examples demonstrate that the administration of compositions comprising either natural or recombinant IFN-γ to patients afflicted with rheumatic disease effected significant and lasting decreases in or elimination of symptoms, such as pain, and led to considerable improvements in the motor responses of those patients. These results were unexpected based upon previous clinical studies of interferons generally and due to prior beliefs that interferon therapy was contraindicated in the treatment of rheumatic diseases.

EXAMPLE 1

In this example, the patient was a 49 year old male who weighed 79 kg and who was 172 cm tall. He had been suffering from severe chronic polyarthritis for more than ten years, his condition leading to deformities of the hands and feet. Upon admission to the hospital for treatment, he was incapable of movement and no improvement in his symptoms had resulted from conventional therapies.

The patient was treated with an aqueous solution comprising 0.1, 0.5 or $1.0 \times 10^6$ I.U./ml natural human IFN-γ, prepared from human leukocytes, mg human serum albumin, 150 milli-molar sodium chloride and phosphate buffer according to Sorensen, *Biochem. Z.*, 21, p. 131 (1909) and *Biochem. Z.*, 22, p. 352 (1909). The concentration of IFN-γ was $0.1-2.0 \times 10^6$/ml.

The patient received subcutaneous injections of the IFN-γ composition according to the following dosage schedule and regimen:

| Treatment Day | Dosage |
| --- | --- |
| 1 | $0.1 \times 10^6$ I.U. |
| 2 | $0.5 \times 10^6$ I.U. |
| 3 | $0.5 \times 10^6$ I.U. |
| 4 | $1.0 \times 10^6$ I.U. |
| 5 | $1.0 \times 10^6$ I.U. |
| 6 | 0 |
| 7 | 0 |
| 8 | $1.5 \times 10^6$ I.U. |
| 9 | $1.5 \times 10^6$ I.U. |
| 10 | $1.5 \times 10^6$ I.U. |
| 11 | $1.5 \times 10^6$ I.U. |

By the 6th day of treatment, the patient had experienced a substantial decrease in pains in the lower extremities. From day 11 of treatment, the patient could walk and climb steps without pain and all tenderness on percussion had disappeared. These improvements lasted without the need for further treatments.

EXAMPLE 2

In this example, the patient was a 54 year old male weighing 75 kg and who was 181 cm tall. At the time of hospitalization, he suffered from severe chronic polyarthritis which led to deformity of both The patient was treated with a natural human IFN-γ composition prepared from human leukocytes as described in Example 1. He received subcutaneous injections of the IFN-γ composition according to the following dosage regimen:

| Treatment Day | Dosage |
| --- | --- |
| 1 | $0.5 \times 10^6$ I.U. |
| 2 | $0.5 \times 10^6$ I.U. |
| 3 | $0.5 \times 10^6$ I.U. |
| 4 | $0.5 \times 10^6$ I.U. |
| 5 | $0.5 \times 10^6$ I.U. |
| 6 | 0 |
| 7 | 0 |
| 8 | $1.0 \times 10^6$ I.U. |
| 9 | $1.0 \times 10^6$ I.U. |
| 10 | $1.0 \times 10^6$ I.U. |

As a result of treatments with $0.5 \times 10^6$ I.U. on days 1-5 of therapy, the amount of pain experienced by the patient decreased progressively. After treatments with $1.0 \times 10^6$ I U. of the IFN-γ composition on days 8-10 of therapy, the patient was entirely free of pain. Before treatment with the IFN-γ composition, the patient could exercise, at most, for 4 minutes on a stationary bicycle. As of the 9th day of treatment, he could exercise on the stationary bicycle twice a day for a period of 20 minutes per exercise trial.

Seventeen days after the start of treatment, the patient was discharged from the hospital. At the time of discharge, he was not experiencing any pain, his mobility was excellent and he was no longer sensitive to percussion over the joints. These improvements lasted without the need for continued treatment. The patient feels well and no longer requires cortisone therapy.

EXAMPLE 3

In this example, the patient, a 37 year old female, weighed 66 kg and was 167 cm in height. She had been diagnosed as suffering from seronegative rheumatic polyarthritis accompanied by anemia, psoriasis and local nodal hyperplasia of the liver.

The patient was treated with an aqueous solution comprising 100 μg/ml recombinant human IFN-γ, 6 mg human serum albumin, 8 mg sodium chloride, 0.2 mg potassium dihydrogen phosphate and 1.4 mg disodium hydrogen phosphate. The concentration of IFN-γ was 100 g/ml. She received intramuscular injections of the recombinant IFN-γ composition according to the following regimen:

| Treatment Day | Dosage |
| --- | --- |
| 1 | 100 μg active substance |
| 2 | 100 μg active substance |
| 3 | 100 μg active substance |
| 4 | 100 μg active substance |
| 5 | 100 μg active substance |
| 6 | 100 μg active substance |
| 7 | 100 μg active substance |
| 8 | 100 μg active substance |
| 9 | 0 |
| 10 | 0 |
| 11 | 175 μg active substance |
| 12 | 175 μg active substance |
| 13 | 50 μg active substance |
| 14 | 50 μg active substance |

During days 1-3 of treatment, the patient experienced an increase in pain. She was free of pain for the first time on the 4th day of therapy. Upon further treatment, the patient experienced some pain for short periods of time. For over one year, the patient continued to receive 10 μg of active substance by intramuscular injection — initially, once a week and subsequently, once every two weeks. She tolerated the treatments well and has not experienced any further pain.

EXAMPLE 4

In this example, the patient was a male suffering from extremely painful myogelosis over a six-month period.

The patient was treated with a natural human IFN-γ composition prepared from human leukocytes, as described in Example 1. He received a single dose, $0.5 \times 10^6$ I.U., of the human IFN-γ composition by intramuscular injection. Within a few minutes of the injection, the patient no longer experienced any pain and he has remained pain free since the treatment.

EXAMPLE 5

In this example, the patient, a 60 year old female, was diagnosed as having established rhematoid arthritis affecting the hands, hips, knees, ankles and metatarsal phalangeal joints. She had suffered from the disease for four years and was non-responsive to therapy with either gold salts or prednisolone.

The patient was treated with a composition comprising recombinant human IFN-γ, as described in Example 3. She received subcutaneous injections of the recombinant IFN-γ composition according to the following treatment schedule:

| Treatment Day | Dosage |
| --- | --- |
| Days 1-16 | 2 injections of 250 μg active substance per injection |
| Days 17-22 | 2 injections of 100 μg active substance per injection |
| Days 23-38 | 1 injection of 100 μg twice a week |

After the first 5 days of treatment, the patient did not experience any pain and she could move about freely. As a result of subsequent maintenance therapy, the clinical picture of rheumatoid arthritis continued to improve and the patient remained free of pain.

EXAMPLE 6

In this example, the patient, a 50 year old female, weighed 68 kg and was 172 cm tall. She had suffered from severe chronic polyarthritis for 19 years. Her symptoms did not respond to treatments with non-steroidal drugs and she did not tolerate gold or penicillamine therapy.

The patient was treated with a composition comprising recombinant human IFN-γ, of Example 3. She received subcutaneous injections of the recombinant IFN-γ composition according to the following regimen:

| Treatment Day | Dosage |
| --- | --- |
| 1-20 | μg active substance |
| 21 + (4 month period) | 20 μg active substance administered twice per week |

After 20 days of treatment, the patient's general symptoms were substantially diminished. A significant decrease in sensitivity of the joints also resulted — as reflected by over an 80% decrease in the Ritchie Index, the articular index for assessment of joint tenderness, measured for the patient. In addition, the level of pain upon movement was reduced by 2.5 WHO degrees.

EXAMPLE 7

In this example, the patient was a female suffering from periarthritis humeroscapularis over a 1 week period. She was treated with a natural human IFN-γ composition prepared from human leukocytes as described in Example 1.

She received a single subcutaneous injection, $0.5 \times 10^6$ I.U., of the IFN-γ composition. Within a few minutes, the patient was free of pain. Since then, the patient has not experienced any further pain.

EXAMPLE 8

In this example, the patient was a male who had been diagnosed as having ischialgia $L_5/S_1$ right (i.e., located at the lumbar 5 and sacral 1 disc of the spine) and osteoporosis over a 3 week period. He was treated with a natural human IFN-γ composition prepared from human leukocytes, as described in Example 1.

The patient received two paravertebral injections of the IFN-γ composition as follows:

| Treatment Day | Dosage |
| --- | --- |
| 1 | $0.5 \times 10^6$ I.U. |
| 21 | $0.5 \times 10^6$ I.U. |

The first injection alleviated the patient's pain over a 5 day period. After the second injection, the patient remained pain-free and to date, nine months after the first treatment, he has not experienced further pain.

EXAMPLE 9

In this example, the patient, a 58 year old female, weighed 49 kg and was 163 cm in height. For four years, she suffered from classic rheumatoid arthritis, as defined by the diagnostic criteria established by the American Rheumatism Association see *The Merck Manual*, supra, p. 2, at 1179).

The patient was treated with a composition comprising recombinant human IFN-γ, of Example 3. She received subcutaneous injections of the recombinant IFN-γ composition according to the following regimen:

| Treatment Day | Dosage |
| --- | --- |
| 1-20 | 50 μg active substance twice daily |
| 21 + | gradual reduction of dosage and frequency of administration to 50 μg active substance administered twice weekly |

After 20 days of treatment, the patient's general symptoms and motor responses clearly improved. The Ritchie Index measured for the patient (see Example 6) decreased from 43 to 33. Pain at rest was reduced by three WHO degrees and pain on movement was reduced by one WHO degree. This improvement has lasted five months up to the present time.

EXAMPLE 10

In this example, the patient, a 60 year old female weighed 61 kg and was 164 cm in height. She suffered from classic rheumatoid arthritis for eleven years.

The patient was treated with a composition comprising recombinant human IFN-$\gamma$, of Example 3. She received subcutaneous injections of the recombinant IFN-$\gamma$ composition according to the following regimen:

| Treatment Day | Dosage |
|---|---|
| 1–20 | 50 µg active substance twice daily |
| 21 + | gradual reduction of dosage and frequency of administration to 50 µg active substance administered twice weekly |

After 20 days of treatment, the patient's general symptoms and motor responses clearly improved. The Ritchie Index measured for the patient (see Example 6) decreased by 35%. Pain on waking, at rest and on motion were each reduced by one WHO degree. This improvement has lasted six months until the present.

EXAMPLE 11

In this example, the patient, a 65 year old female, weighed 65 kg and was 160 cm tall. For ten years, she suffered from definite rheumatoid arthritis, as defined by the diagnostic criteria established by the American Rheumatism Association (see *The Merck Manual*, supra, p. 19).

The patient was treated with a composition comprising recombinant human IFN-$\gamma$, of Example 3. She received subcutaneous injections of the recombinant IFN-$\gamma$ composition according to the following regimen:

| Treatment Day | Dosage |
|---|---|
| 1–20 | 50 µg active substance twice daily |
| 21 + | gradual reduction of dosage and frequency of administration to 50 µg active substance administered twice weekly |

After 20 days of treatment, the patient's general symptoms and motor responses clearly improved. The Ritchie Index measured for the patient (see Example 6) decreased by 40%. The patient's grip strength was improved and the duration of morning stiffness decreased. This improvement has lasted for four months until the present time.

EXAMPLE 12

In this example, the patient, a 44 year old male, weighed 72 kg and was 183 cm in height. He suffered from definite rheumatoid arthritis for eight months.

The patient was treated with a composition comprising recombinant human IFN-$\gamma$, of Example 3. He received subcutaneous injections of the recombinant IFN-$\gamma$ composition according to the following regimen:

| Treatment Day | Dosage |
|---|---|
| 1–20 | 50 µg active substance |
| 20 + | 50 µg active substance administered three times a week |

After 20 days of treatment, although the patient showed no improvement in clinical symptoms, his blood sedimentation rate ("BSR") was reduced from 130 mm to 66 mm (read after one hour). During the continued course of therapy, the BSR decreased further, the patient's motor responses improved and the patient's morning stiffness decreased. As a result of this treatment, the patient was able to return to work. The improved has lasted four months up to the present time.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A process for treating rheumatic diseases comprising the step of administering to a mammal a pharmaceutically acceptable composition which comprises a pharmaceutically effective amount of IFN-$\gamma$.

2. The process according to claim 1, wherein the IFN-$\gamma$ is selected from the group consisting of natural IFN-$\gamma$, recombinant IFN-$\gamma$, and derivatives thereof which are characterized by the biological activity of IFN-$\gamma$ against rheumatic diseases.

3. The process according to claim 1, wherein the rheumatic disease to be treated is selected from the group consisting of inflammatory rheumatism, degenerative rheumatism, extra-articular rheumatism and collagen diseases.

4. The process according to claim 1, wherein the rheumatic disease is selected from the group consisting of rheumatoid arthritis, systemic lupus erythematosus, progressive systemic schleroderma, dermatomyositis, chronic polyarhritis, psoriasis arthropathica, muscular rheumatism, periarthritis humeroscapularis, panarthritis nodosa, arthritis uratica, myositis, myogelosis, chondrocalcinosis and juvenile chronic arthritis.

5. The process according to claim 1, wherein the mammal is a human.

6. The process according to claim 1, wherein the composition which comprises IFN-$\gamma$ further comprises a compound selected from the group consisting of interferons other than IFN-$\gamma$, interluekin-1, interleukin-2, tumor necrosis factor, macrophage colony stimulating factor, macrophage mirgration inhibitory factor, lymphotoxin, fibroblast growth factor, thymus hormones and conventional anti-rheumatic therapeutic agents.

7. The process according to claim 1, wherein the composition is administered intravenously, intramuscularly, subcutaneously, intra-articularly, intrasynovially, intrathecally, periostally, by infusion, orally or topically.

8. The process according to claim 1, wherein the composition is administered at a dosage of between 200 International units (20 ng) and 2000 million International units (200 mg).

9. The process according to claim 8, wherein the dosage is between 20,000 International units (2 μg) and 2,000,000 International units (200 μg).

* * * * *

UNITED STATES PATENT AND TRADEMARK OFFICE
CERTIFICATE OF CORRECTION

PATENT NO. : 4,946,674

DATED : August 7, 1990

INVENTOR(S) : Johann-Friedrich von Eichborn, Hans-Joachim Obert and Franz Link

It is certified that error appears in the above-identified patent and that said Letters Patent is hereby corrected as shown below:

Column 6, line 9, delete "(10 mg)" and insert therefor -- (200 mg) --;
    line 26, delete "1" and insert therefor -- I --;
    line 68, delete "106" and insert therefor -- $10^6$ --.

Column 8, line 2, after "both", insert -- hands --;
    line 21, delete "106" and insert -- $10^6$ --;
    line 46, delete "6" and insert therefor -- 5 --;
    line 50, delete " g/ml" and insert therefor -- ug/ml --.

Column 9, line 66, before "ug", insert -- 50 --.

Column 12, line 22, delete "improved" and insert therefor -- improvement --;
    line 51, delete "schleroderma" and insert therefor -- scleroderma --;
    line 52, delete " polyarhritis" and insert --polyarthritis--.
    line 63, delete "mirgration" and insert therefor -- migration --.

Signed and Sealed this

Thirtieth Day of November, 1993

Attest:

BRUCE LEHMAN

Attesting Officer    Commissioner of Patents and Trademarks